US005362302A

United States Patent [19]

Jensen et al.

[11] Patent Number: 5,362,302

[45] Date of Patent: Nov. 8, 1994

[54] THERAPEUTIC TABLE

[75] Inventors: Robert J. Jensen, Stewartville; Thomas J. Liebl; David J. Liebl, both of Donnelly, all of Minn.

[73] Assignee: Jensen Three In One, Stewartville, Minn.

[21] Appl. No.: 207,889

[22] Filed: Mar. 7, 1994

Related U.S. Application Data

[63] Continuation of Ser. No. 544,825, Jun. 27, 1990, abandoned.

[51] Int. Cl.[5] .......... A61F 5/00

[52] U.S. Cl. .......... 601/24; 606/242; 606/241; 5/612; 5/618

[58] Field of Search .......... 606/238, 240–245; 5/600, 608, 612–613, 618, 652, 658; 482/118, 139, 113, 114; 601/5, 23, 24–26, 33

[56] References Cited

U.S. PATENT DOCUMENTS

| | | | |
|---|---|---|---|
| 1,166,018 | 12/1915 | Soresi . | |
| 1,400,546 | 12/1921 | Holme . | |
| 1,582,950 | 5/1926 | Weaver et al. | 606/245 |
| 2,284,445 | 5/1942 | Pettit . | |
| 2,577,177 | 12/1951 | Anderson | 5/600 |
| 2,623,518 | 12/1952 | Vaquette . | |
| 2,695,017 | 2/1954 | Herrmeyer . | |
| 2,707,465 | 5/1955 | Nemeth . | |
| 2,764,150 | 9/1956 | Ettinger . | |
| 3,160,381 | 12/1964 | Langbaum . | |
| 3,302,641 | 2/1967 | Berne . | |
| 3,643,938 | 2/1972 | Levasseur . | |
| 3,707,963 | 1/1973 | Keropian . | |
| 3,754,749 | 8/1973 | Lyon et al. . | |
| 3,771,518 | 11/1973 | Greissing . | |
| 3,916,882 | 11/1975 | Jameson . | |
| 3,941,365 | 3/1976 | Frymoyer . | |
| 4,061,137 | 12/1977 | Sandt . | |
| 4,379,450 | 4/1983 | Sjölinder . | |
| 4,582,311 | 4/1986 | Steffensmeier . | |
| 4,602,618 | 7/1986 | Berzé5 | 658 X/ |
| 4,603,856 | 8/1986 | Fiore | 482/114 |
| 4,722,328 | 2/1988 | Scott et al. . | |
| 4,733,859 | 3/1988 | Kock et al. . | |
| 4,872,657 | 10/1989 | Lüssi . | |

*Primary Examiner*—Richard J. Apley
*Assistant Examiner*—Linda C. M. Dvorak
*Attorney, Agent, or Firm*—Vidas, Arrett & Steinkraus

[57] ABSTRACT

A therapeutic table for manipulation of the spine and pelvis of a patient supported thereon. The table includes a tiltable frame mounted to a base, and a torso support member carried by the frame. A drive shaft carried by the frame is connected by a hinge to a driven shaft extending rearwardly of the torso support member. The driven shaft in turn carries a pelvic/lumbar spine support member on which a patient may kneel. When the hinge connecting the two shaft portions is adjusted to a non-zero angle, rotation of the shaft induces a circumductive motion in the pelvic/lumbar spine support member, the degree of such motion being dependent on the angle of the hinge.

37 Claims, 5 Drawing Sheets

THERAPEUTIC TABLE

This is a continuation of copending application Ser. No. 07/544,825 filed on Jun. 27, 1990, now abandoned.

FIELD OF THE INVENTION

The invention relates to an automated therapeutic table useful in the treatment, excercise and manipulation of the spine, such as chiropractic or physical therapy treatment.

BACKGROUND ART

The science of chiropractic involves the selective adjustment of any abnormal articulations of the human body, especially those of the spinal column, for the purpose of assuring full and free range of motion, and freeing impinged nerves that may cause pain or deranged function. Careful, skilled manipulation of the spine, therefore, is central to effective chiropractic treatment.

Moreover, to maintain the condition of the spine and the tone of the contiguous soft tissue structures, it is often advantageous to manipulate the spine to achieve better alignment of its component parts. Typically this manipulation is done manually by a therapist with the patient lying on his or her abdomen or back. For example, with a patient lying on his abdomen, the therapist may attempt to realign a vertebra by imparting a manual force to it while holding the adjacent vertebra stable. This technique, while frequently effective, is highly dependent on the therapist's physical strength and skill in performing the manipulation, and is limited by physical constraints including the size and health of the patient and the inherent fact that the spine is in a static condition (i.e., is oriented in a generally fixed, unmoving position as the patient lies on the treatment table).

It is also advantageous to treat injuries to and conditions of the spine by having the patient perform various exercises in an active/passive regime designed to achieve better alignment of the spine and tone of adjacent soft tissue structures, i.e., nerves, muscles, ligaments, tendons and blood and lymphatic circulation. Again, however, such excercise is limited by the patient's physical strength and coordination, and other factors that may inhibit the proper excercise needed, both in terms of degree and direction of movement and duration of the excercise.

SUMMARY OF THE INVENTION

The invention provides a therapeutic table upon which a patient may be supported. The table includes separate parts which support different portions of the patient's body, the parts being movable relative to one another in a predetermined fashion so as to impart specific predetermined motions to the patient's body, i.e., to flex, extend, circumduct, laterally flex, and longitudinally extend and compress the spine in a continuous controlled and rhythmic manner. The table is motorized to facilitate oscillatory relative movement between the parts of the table, thereby motioning the patient's spine in a controlled manner. The degree of oscillatory relative movement between the parts of the table is selectively adjustable according to the specific patient's needs.

To those ends, tile present invention comprises a therapeutic table having a member supporting the patient's pelvic area and lumbar spine and a separate member supporting the patient's upper torso and cervical spine. The supporting members are mounted to a base and are arranged in a fashion such that the patient will be laying in a kneeling position with his legs and knees at a generally 90 degree angle. The upper torso/cervical spine member is supported upon a telescoping, generally horizontal bracket such that the position of the upper torso/cervical spine member may be moved in a generally horizontal direction with respect to the primary circumductive movement produced by the pelvic/lumbar spine member. The pelvic/lumbar spine member bracket is attached to the base in such a fashion that it may be pivoted in a horizontal plane about a vertical axis as well as about a transversely extending horizontal axis.

The pelvic/lumbar spine member comprises a generally horizontal surface upon which a patient can kneel and a generally vertical surface against which tile patient's thighs may be placed in abutment. The opposite side of the vertical portion is operatively connected to a drive motor through an adjustable articulated shaft such that rotation of the shaft by the motor will impart circumducting motion to the pelvic/lumbar spine member. Rotation of the shaft upon operation of the motor when the patient is in place will thus provide controlled varying degrees of oscillating lateral flexion, rotation and extension/compression motions to the patient's spine. The degree of articulation of the shaft is selectively adjustable to increase or decrease the degree of such motion according to the specific needs of the patient.

DETAILED DESCRIPTION OF THE PREFERRED EMBODIMENT

Figure 1:
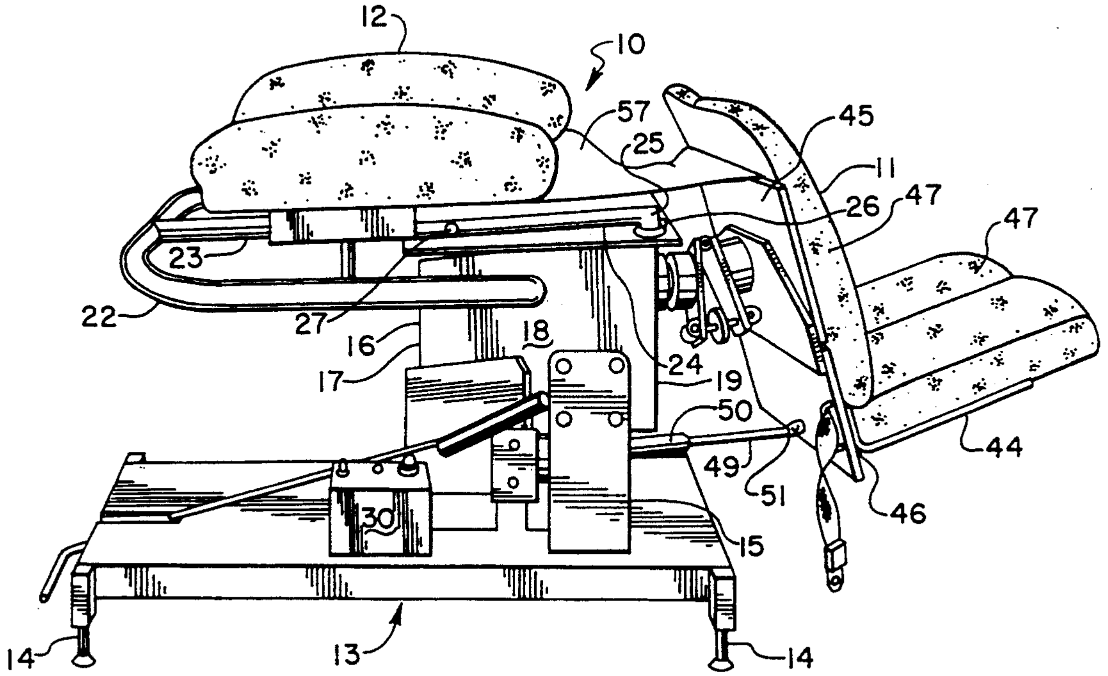
FIG. 1 is a side view of a therapeutic table according to the present invention.
Figure 6:
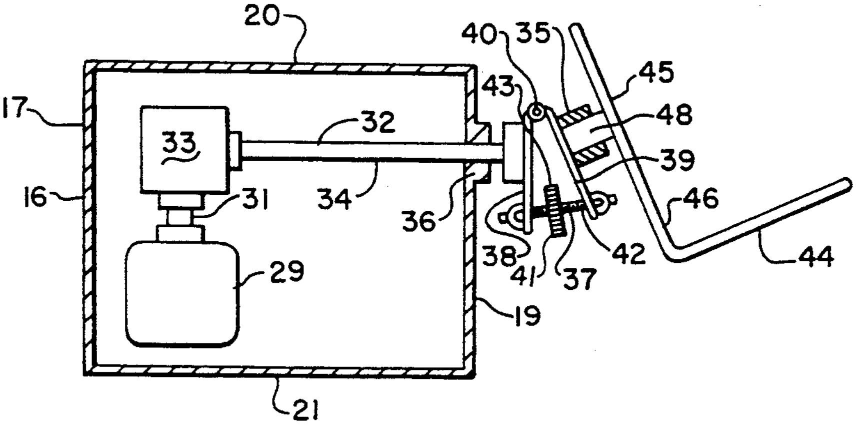
FIG. 6 is a schematic view of the drive train of one embodiment of the present invention.
Figure 2:
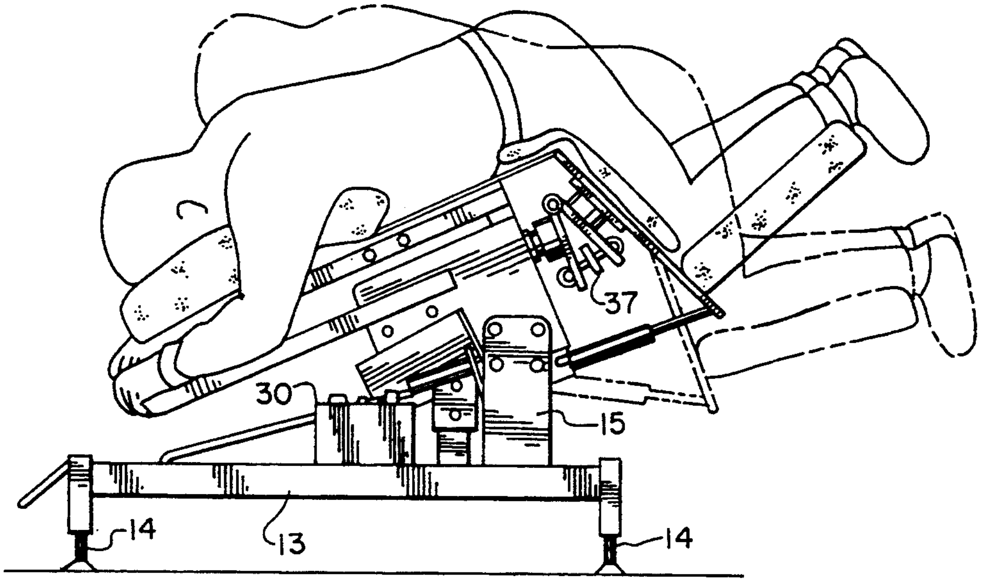
FIG. 2 is a side view of a therapeutic table according to the present invention illustrating a patient using the device.

Referring to FIGS. 1-6 which show one embodiment of the invention, a therapeutic table generally designated 10 is designed to support a patient ::in a generally prone horizontal position with his knees brought up as seen in FIG. 2. The table 10 includes a pelvic/lumbar spine support member 11 and an upper torso/cervical spine support member 12 supported by a generally rectangular base 13. The base 13 preferably has level adjusting legs 14 at each corner and a pair of spaced, upwardly extending supports 15.

A housing 16 having front, side and rear portions 17, 18 and 19, respectively, is pivotally supported by the supports 15, one each of the supports 15 being attached to a side portion 18 of the housing 16 in such a fashion that the housing 16 may be tilted forwardly from the position shown in FIG. 1 to a position shown in FIG. 2. Such adjustment may be accomplished by any suitable mechanism. In a preferred embodiment a screw drive may be connected between the housing 16 and the base, the screw drive being oriented generally longitudinally of the table so that as the screw turns it urges a bracket attached to the housing forward or backward to tilt the housing the desired amount. The screw drive may be operated manually or may be motorized. In a particularly preferred embodiment the screw drive is motorized and is activatable by a foot switch so that the therapist may adjust the degree of tilt easily during the treatment.

The upper torso/cervical spine support member 12 preferably is mounted to the housing 16 in a fashion that permits such support member 12 to rotate horizontally from side to side about a generally vertical axis (i.e., vertical when the table is in the position depicted in FIG. 1). In a preferred embodiment, the support member 12 includes a generally U-shaped bracket 22 having a centered, rearwardly received within (or over) a tubular member 24 having a downwardly dependent rearward end 25 which is received in a generally circular collar 26 formed in the rear center of the top 20 of the housing 16. One or more threaded locking bolts 27 may be provided extending through threaded holes in the tubular member 24 to frictionally lock the leg 23 in desired relation to tubular member 24. In this fashion, it will be seen that the upward torso/cervical spine support member 12 is longitudinally movable with respect to the table 10. It is also noted that the member 12 may be rotated to either side by rotation of the leg 23 within the tubular member 24. Similarly, a threaded locking bolt 28 may be provided extending through a threaded hole in the collar 26 to frictionally lock the rearward end 25 of the tubular member 24 in desired relation to the collar 26 and thus the housing 16. In this fashion, it will be seen that the upper torso/cervical spine support member 12 is selectively angularly positionable in a generally horizontal plane with respect to the center line of the table 10. That is, the support member 12 may be rotated from side to side to induce lateral flexion in the spine of the patient. Any other conventional locking mechanism similarly may be provided to secure the support member 12 in a central, left or right oriented position. In one particularly preferred embodiment a bearing carried between the support member 12 and the top of the housing 16 helps support the torso/cervical spine support member 12 on the housing and normally rests in a complementary depression, thereby normally restraining such support member 12 in the central position unless it is actively pushed left or right out of such position by the therapist.

Figure 7:
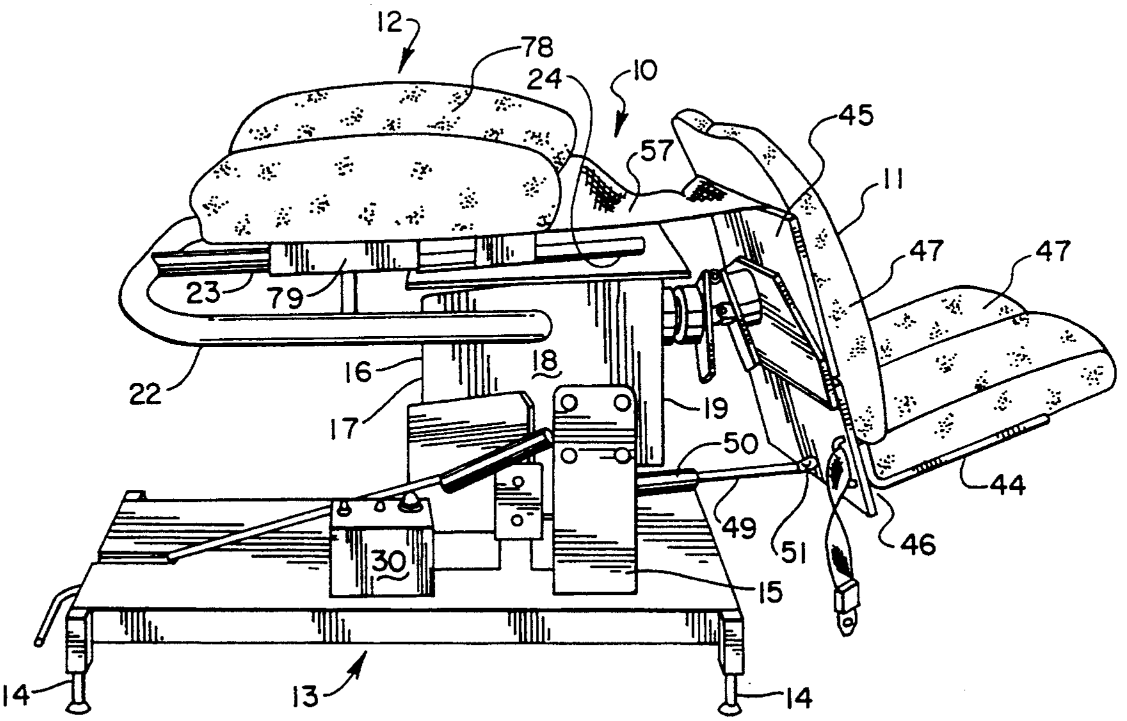
FIG. 7 is a side view of an alternate embodiment of a table according to the invention.

In an alternate embodiment shown in FIG. 7, the padded portion 78 of the torso/cervical member is mounted to the tubular member 24 by rails 79 that permit free relative longitudinal movement of the padded portion 78 with respect to the tubular member 24 and the U-shaped bracket 22; this configuration allows the patient's torso to glide longitudinally as the pelvic/lumbar support member 11 rotates circumductively. Such movement also allows the patient to place his spine in traction or compression by alternately pushing or pulling on the U-shaped bracket 22 as the pelvic/lumbar support member rotates.

Referring again to FIGS. 1–6, mounted within the housing 16 is a motor 29 (shown diagrammatically in FIG. 6) operated through controls 30 having an upwardly extending output shaft 31. The output shaft 31 is operatively connected to a rearwardly extending articulated drive shaft 32 through a suitable gear 33. The drive shaft 32 comprises a first portion 34 extending from gear 33 rearwardly through a bearing 36 fixed in the rear 19 of the housing 16, to a second member 35 attached to the pelvic/lumbar spine support member 11 in a manner hereafter described. The first member 34 and the second member 35 of the drive shaft 31 are articulately joined by hinge 40 and adjusting mechanism 37 such that axial rotation of the first member 34 will impart a circumducting motion to the second member 35.

Figure 3:
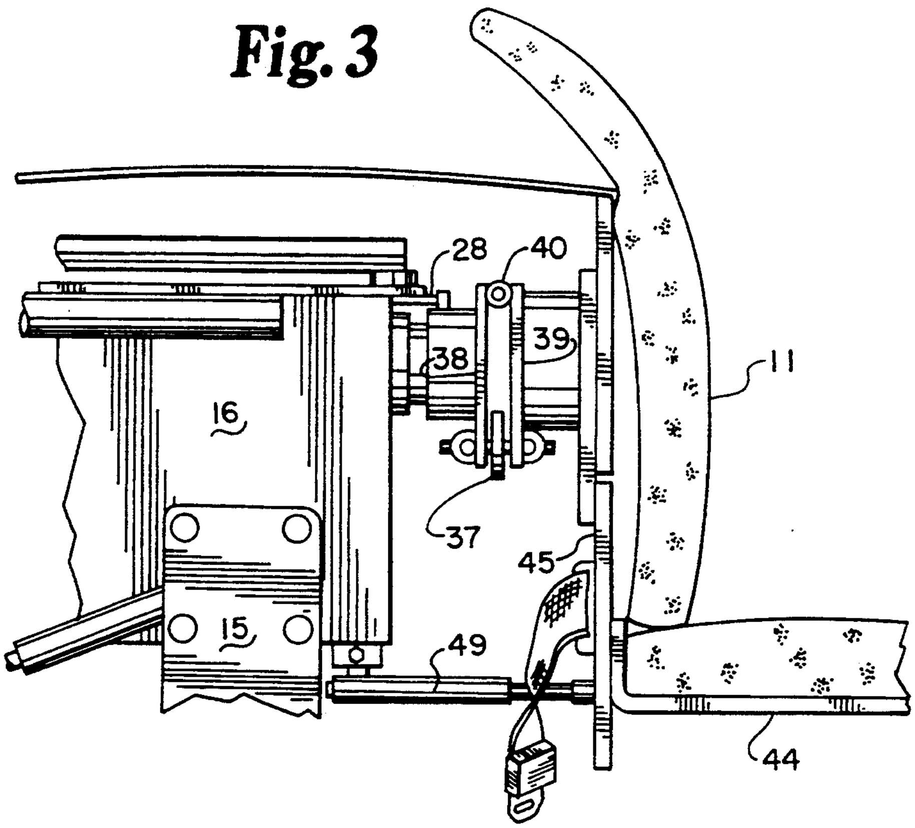
FIG. 3 is a fragmentary side view illustrating one adjusting mechanism of the present invention at a first degree of adjustment.
Figure 4:
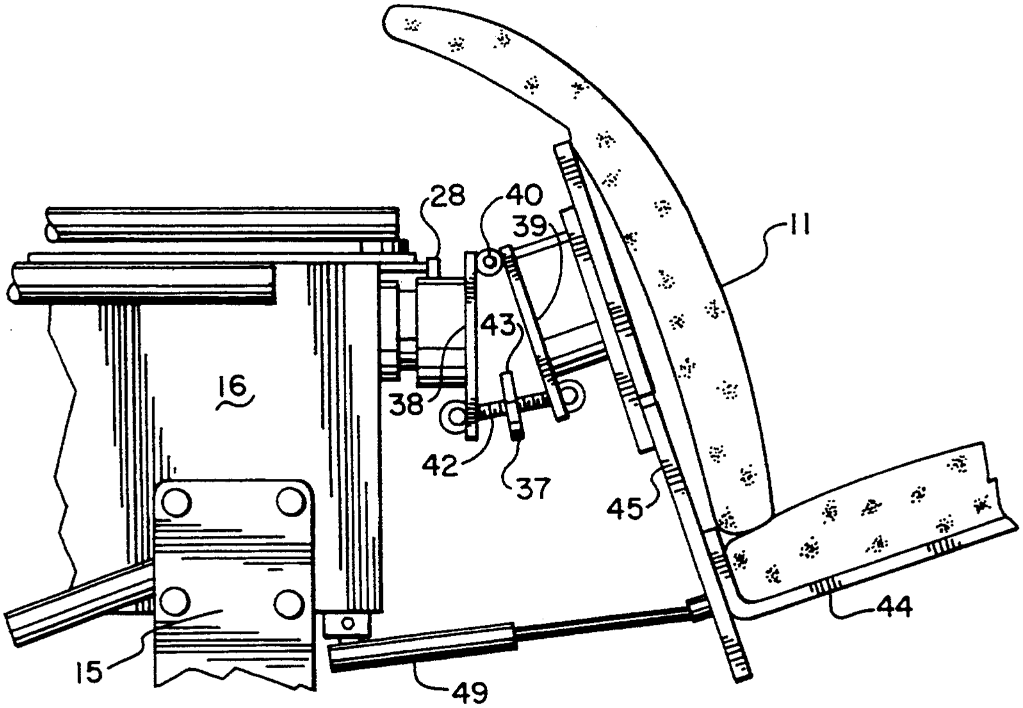
FIG. 4 is a fragmentary side view illustrating the adjusting mechanism of FIG. 3 at a second degree of adjustment and further illustrating the relative position of the pelvic/lumbar spine member of the present invention at one point along its oscillatory path.
Figure 5:
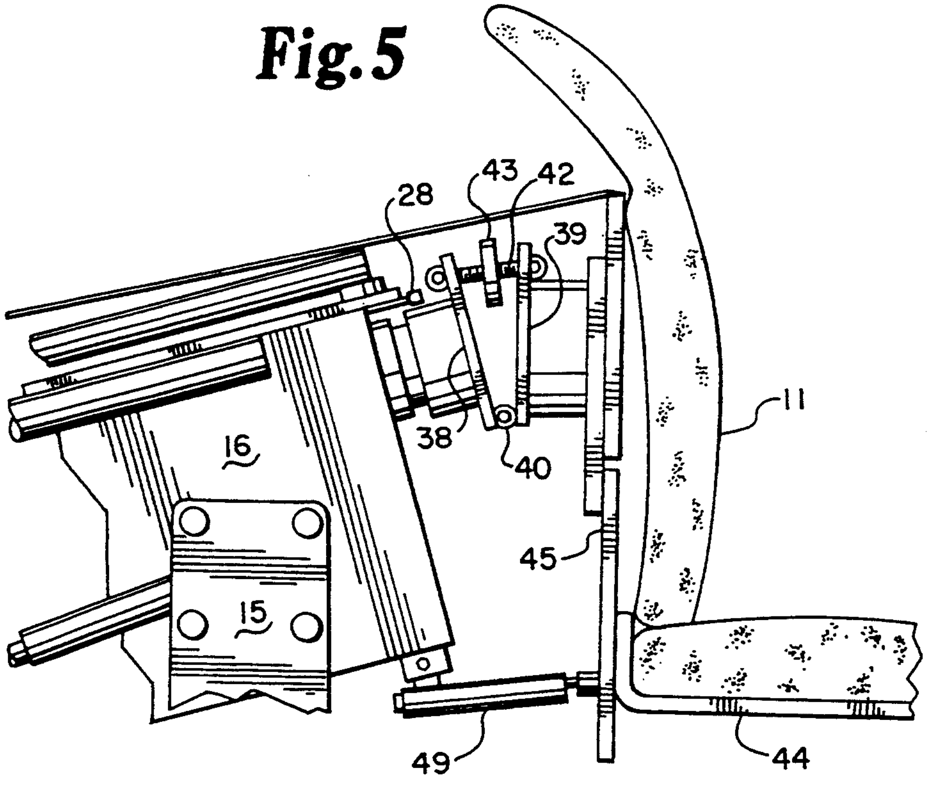
FIG. 5 is a fragmentary side view illustrating the second degree of adjustment shown in FIG. 4 with the pelvic/lumbar spine member at a second point along its oscillatory path.

The hinge 40 comprises a first plate 38 fixed, as by welding, to the rearward end of the first member 34 and an adjacent second plate 39 fixed to the forward end of the second member 35. The plates 38, 39 are hingedly attached at one end by a conventional hinge pin. The adjustment mechanism for setting the angle (or "throw-out") of the hinge may comprise any effective mechanism that allows selective adjustment. In the embodiment of FIGS. 1–6, the mechanism comprises an adjustable spacer 41. The adjustable spacer 41 is adjustable to either draw the opposite ends of the plates 38, 39 together (as seen in FIG. 3) or to drive such ends apart (as seen in FIGS. 4, 5). In one embodiment the spacer 41 comprises a right and left opposing threaded bolt 42 having opposing ends which are matingly received in threaded holes formed in each of the plates 38, 39, said bolt 42 carrying a manually rotatable, centrally positioned disk 43 keyed or fixed to the bolt 42 such that by manually rotating the disk 43 in the appropriate direction the ends of the plates 38, 39 opposite the hinge 40 will be either drawn together or driven apart.

Figure 9:
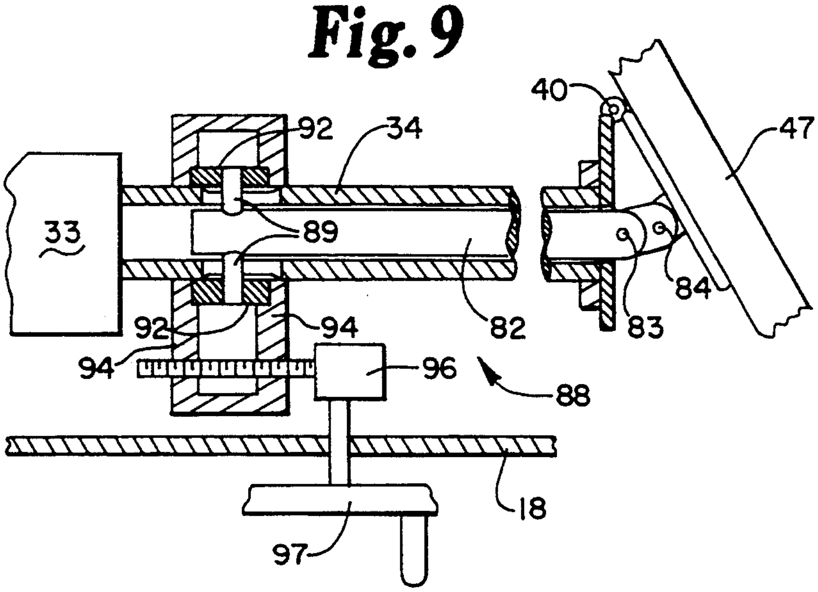
FIG. 9 is a top view of yet another drive train embodiment of the invention.

In an alternate embodiment shown in FIG. 9 the adjusting mechanism is configured to allow easy adjustment of the "throw-out" or angle of the hinge during operation of the table. In this embodiment the first portion 34 of the articulated shaft includes a hollow bore that extends at least partway through the shaft 34 (on the end adjacent the hinge 40). A throw-out rod 82 is closely received in the bore. A first end 83 of the throw-out rod 82 is attached by a pair of pivotable joints 83 and 84 to the second plate 39 of the hinge (i.e., the plate to which the pelvic/lumbar support member is attached). The pivotable nature of these joints accomodates the arcuate movement of the second plate 39 as the angle is opened and closed.

The second, opposite end 87 of the throw-out rod 82 is connected to a throw-out adjusting mechanism designated generally as 88 (FIG. 9). A pin 89 carried by this second end 87 of the rod 82 extends through slots 90 in the hollow shaft 34. The pin is then secured, as by a friction interference fit or other suitable means, to a drive collar 92. The throw-out rod 82, pin 89, and thrust collar 92 all rotate with the shaft 34, but are slidable longitudinally with respect to the shaft 34. A thrust housing 94 carried about the shaft 34 captures the thrust collar 92, but does not rotate with the collar—rather, it is secured against rotation but is slidingly received over the shaft 34, so that it slides longitudinally with the thrust collar. The thrust housing 94, in turn, is connected through a suitable mechanism such as an appropriate screw drive 95 and gear box 96 to a crank handle 97.

As the handle 97 is rotated in one direction or the other, the screw drive 95 will advance or retract the thrust housing 94 which in turn will advance or retract the thrust collar 92, pin 89 and throw-out rod 82, thereby adjusting the angle of throw-out of the hinge 40. This mechanism is particularly advantageous because it allows the therapist to gradually increase the degree of throwout (circumduction) during a treatment session without requiring the patient to get off the table and without even stopping the circumducting motion of the table. For example, the therapist can begin treatment at a very gentle, slight angle (or even at a zero degree angle), and then gradually increase the angle as the patient becomes accustomed to the motion and relaxed sufficiently to permit increase in the angle. Moreover, if the angle is decreased to zero, (i.e., the axes of the first and second portions 34 and 35 of the shaft 32 are the same), substantially no motion is transmitted to the table even hen the shaft 32 is rotating, allowing the patient to mount or de-mount the table without needing to shut the motor off. Furthermore, mounting and demounting the table is made easier when the angle is decreased to zero.

Figure 8:
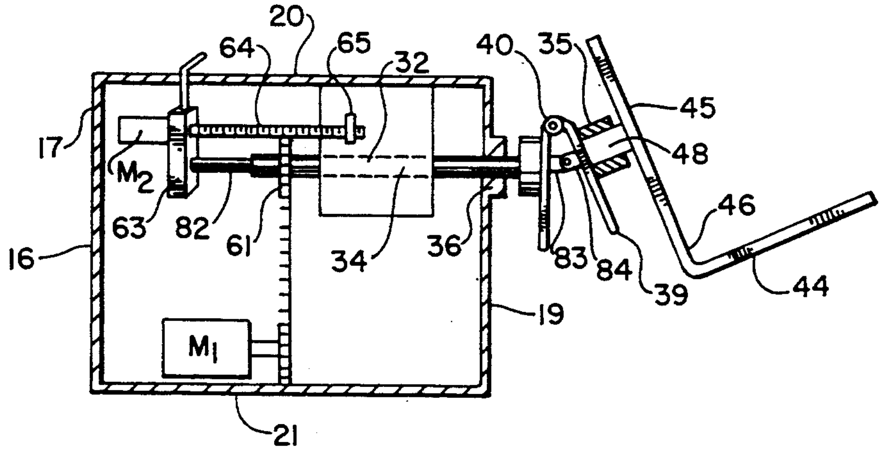
FIG. 8 is a schematic side view of the drive train of the embodiment of FIG. 7.

FIG. 8 depicts ye another embodiment (which is particularly preferred) in somewhat schematic form for adjusting the degree of throw-out and therefore the angle of the pelvic/lumbar support member. In this drawing the motor $M_1$ drives a chain 60 which in turn drives sprocket 61 affixed to hollow shaft 34. Concentric throw-out rod 82, which is slidably received within hollow shaft 34, extends beyond the left end of shaft 34, and is there attached to a throw-out mechanism which operates similarly in principle to the mechanism shown in FIG. 9. A bracket 63 is attached to the end of the rod 82 by means of a bearing or ball joint (not shown for purposes of clarity) which allows the rod 82 to rotate with respect to the bracket but prevents longitudinal movement of the two parts with respect to one another. A screw drive 64 carried by the bracket 63 is driven by a motor $M_2$; the screw drive 64 in turn engages a threaded bracket 65 carried by the housing. As tile screw drive turns, it moves the bracket 63 and the attached throw-out rod 82 longitudinally with respect to the shaft 34, thereby opening or closing the angle of circumduction of the pelvic/lumbar support member 11.

In this embodiment, if the diameter of the throw-out rod 82 is substantially equal to the inner diameter of the hollow shaft 34, then pivot joints 84 and 85 are provided to accommodate the arcuate movement of the second plate 39 of the hinge. Alternately, in a particularly preferred embodiment, the diameter of the throw-out rod 82 is substantially smaller than the inner diameter of the hollow shaft 34, permitting a single pivotal attachment to the second plate 39 of the hinge. In such a configuration the arcuate movement of such plate 39 is accommodated by differences in such diameters, and the opposite end of the rod 82 is attached by a ball joint or similar union to the bracket 63 to allow slight circumductive movement of the rod 82.

Referring further to FIG. 8, the bracket 63 may be configured substantially as shown, or, in another preferred embodiment, the bracket may be somewhat elongated in the direction perpendicular to the page with one end thereof being pivotably attached to the housing (or similar supporting structure). As the total throw (i.e., axial movement) of the throw-out rod 82 is only a few centimeters, so long as the throw-out rod 82 is of a smaller diameter (as described in the preceeding paragraph) and its end is attached to the bracket 63 by a ball joint or similar union, the slight misalignments due to the arcuate movement of the bracket 63 (and the arcuate movement of the second plate 39 of the hinge) do not inhibit proper operation of this mechanism.

As shown in FIG. 8, a throw-out indicator 67 may be attached to the bracket 63 to give a visual indication of the degree of throw-out; for convenience a visual scale may be applied to the adjacent exterior of the housing, giving the therapist an objective measurement of the degree of throw-out at any given time. This is particularly useful for repeating treatment of a patient at the same degree of throw-out.

Both the motor $M_2$ controlling the degree of throw-out and the motor $M_1$ driving the shaft 34 can be controlled by conveniently placed electronic controls, such as 30. In a preferred embodiment, the motor $M_2$ can also be controlled by a conveniently placed foot switch, allowing the therapist to easily change the amount of throw-out, and therefore the degree of circumductive motion, during treatment.

Referring again to FIGS. 1–6, the pelvic/lumbar spine support member 11 is generally "L" shaped having a generally horizontal portion 44 and a generally vertical portion 45. Preferably a piece of elastic material 57, such as Lycra, is attached as shown in the drawings. This material serves both to shield the patient somewhat from the moving parts of the table and also acts to somewhat stabilize the torso/cervical member 12 with respect to the pelvic/lumbar member 11 in the embodiment that allows relative free sliding movement of the torso/cervical member 12.

In one embodiment the pelvic/lumbar spine support member 11 comprises a rigid frame 46 having padding 47 on those areas in which the patient comes in contact. The forward surface of the vertical portion 45 has a forwardly extending cylindrical protrusion 48 which is matingly received within an axial hole of similar size formed in the rearward end of the second member 35 of the drive shaft 32. The projection 48 is secured in mating relation to the second member 35 against axial movement in any conventional fashion, but the second member 35 is free to rotate about its axis. Thus, the projection 48 acts as a journal and the second member 34 a journal bearing. Alternatively, the vertical portion 45 could be provided with a journal bearing with the second member 35 of the drive shaft 32 acting as a journal within the scope of my invention.

Figure 10:
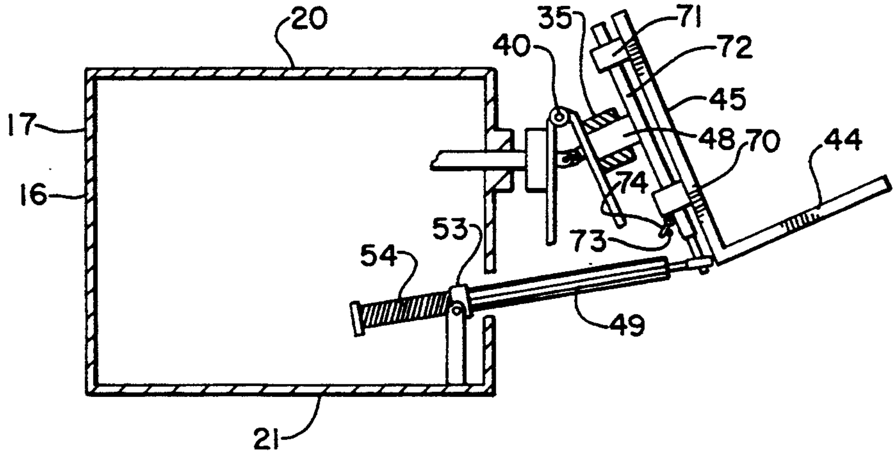
FIG. 10 is a partially broken-away, side view of yet another embodiment of the invention.

A limit rod 49 (omitted from FIGS. 6 and 8 for the sake of clarity) slideably received in a tubular member 50 attached to the bottom 21 of tile housing 16 is attached by a universal joint or knuckle 51 to the bottom of the forward surface of the vertical portion 45. Tubular member 50 may be elongated, as shown in the drawings, or it may be shorter, more approximating a collar 53 (as is shown in FIG. 10). If such a collar 53 is employed, desirably limit rod 49 is stabilized against left/-right movement; for example, such stabilization may be accomplished by having the limit rod 49 extend substantially through the collar 53 and then attaching it to one or more coil springs 54 (or other suitable stabilizing structure) to resist the rotational forces of the circumducting motion. In a particularly preferred embodiment, two coil springs such as that shown in FIG. 10 are provided, one on each side of the limit rod 49. The limit rod 49 therefore limits the direction of movement of the bottom portion of the pelvic/lumbar spine support member 11 upon rotation of the drive shaft 32.

In a preferred embodiment shown in FIG. 10 the pelvic/lumbar support member includes an adjustable frame 70 that is adjustable vertically to accomodate patients of different heights. Such adjustability may be accomplished through any desired mechanism. For example, the frame 70 may be attached to collars 71 that slide vertically on posts 72. Alternately, mating telescoping tubes (square or round or other configurations) might be used. In yet a further variation, the pelvic/lumbar support member may be constructed so that only the horizontal portion 44 is vertically adjustable, the vertical portion 45 being fixedly mounted. In either case, the adjustable part may be fixed in its position by suitable bolts or pins extending through one or more of the collars 71 into complementary holes in the posts 72, or by any other convenient mechanism. In a preferred embodiment having at least two generally vertically oriented posts 72, a pair of pins 73 (one for each post) are carried on a transversely oriented bar 74 which is pivotable between a first position (shown in FIG. 10) where the pins are retracted (i.e., disengaged) and a second position where the pins are inserted into complementary holes in the posts 72. The bar 74 preferably is spring loaded to urge the pins into the posts.

In operation, the patient is placed upon the table in essentially tile same position as shown in FIG. 2 with his knees and lower legs resting on the generally horizontal portion 44 and his thighs in abutment against the generally vertical portion 45. The patient's upper torso and face are supported in the upper torso/cervical spine support member 12 in the manner illustrated. The upper torso/cervical spine support member 12 may be longitudinally adjusted with respect to the table to accommodate the specific patient's height, and preferably is freely movable along rails 79 (as shown in FIG. 7). In addition, the upper torso/cervical spine support member 12 may be rotated either axially of the leg 23 or in a horizontal plane about a vertical axis according to the specific needs of the patient, and the position of the U-shaped bracket 22 may be adjusted to the patient's size and desires. Once the proper location of these parts is determined and the patient is confortably positioned on the table, the table may be tipped forward or backward on a pivot attached to a base. Such adjustment preferably is accomplished by the therapist activating a foot switch (or other conveniently located switch) to activate a motor attached to the tilt adjustment screw drive.

Upon operation of the main motor 29 rotation of the drive shaft 32 commences. The degree of throw-out may then be adjusted (by turning the manual crank 97 or activating the motor $M_2$) to commence circumductive rotation of the pelvic/lumbar spine support member (if the configuration of FIG. 1 is used, desirably the disk 43, which adjusts the degree of opening of the hinge 40, is adjusted before the motor is turned on).

In a preferred embodiment emergency stop switches may be mounted in a location convenient for the patient to activate should he desire for any reason to immediately stop all function of the table. Though not shown for purposes of clarity of the drawings, a preferred location for such switches is on either side of the torso/cervical support member 12 immediately below the padded portion 78; desirably the switches are connected to large activation bars or tabs that are easy for the patient to depress.

The patient's lumbar spine and pelvis—and to a lesser extent the thoracic and cervical spine-will be thereby manipulated in a circumducting movement. Such movement provides oscillatory lateral flexion, rotation and longitudinal extension/compression to the spine, all with advantageous therapeutic effects to the patients. Such motion is believed to help realign the vertebrae, particularly in connection with simultaneous manipulation of the vertebrae, and is believed induce a pumping action in the blood, lypmphatic and spinal fluids which helps relieve trapping of such fluids, nerve roots and attendant disorders of the musculoskelatal and nervous systems. The degree of circumducting motion can be regulated to fit the needs of each specific patient.

As the patient is so moved the therapist may conduct a variety of treatment manipulations. For example, as the spine is rotated through the circumductive motion, the therapist may exert force on a vertebra to immobilize it; the table will induce the required force on he adjacent vertebra, thereby accomplishing the desired adjustment. This treatment mechanism therefore allows careful control over the degree of force exerted, and facilitates effective treatment by the therapist.

While I have described the preferred embodiment of my invention, it will be apparent to those of ordinary skill in the art that other embodiments are possible within the spirit of my invention and the scope o the following claims.

What is claimed is:

1. A therapeutic table for manipulation of the spine and pelvis of a patient supported thereon, comprising:

a base;

an upper torso/cervical spine support member supported on the base;

an articulated shaft having a first member, mounted to the base for rotation about a fixed axis, and a second member;

a hinge joining the first member and the second member, and adjustment means for adjusting the relative angle between the axis of the first member and the axis of the second member of the shaft;

a pelvic/lumbar spine support member rotatably attached to the second member of the shaft; and means for rotating the first member of the shaft about a fixed axis so that when the adjustment means is adjusted to a non-zero angle between the axes the second member of the articulated shaft and the associated pelvic/lumbar support member move in a circumductive motion.

2. The therapeutic table of claim 1 wherein the hinge comprises a pair of plates hinged along one edge, the plates being respectively attached to abutting ends of the first and second members, and the adjustment means comprising an adjustable spacer positioned between the plates.

3. The therapeutic table of claim 1 wherein the first member of the shaft has an axial bore at least partially therethrough, and the adjustment means comprises a rod slidably disposed in the bore, the rod being operatively attached at a first end to the second member of the shaft and including means for adjusting the longitudinal position of the rod with respect to the first member of the shaft to thereby adjust the angle between the axes of the shaft members.

4. The therapeutic table of claim 1 including pivot mounting means for mounting the torso/cervical spine support member and the pelvic/lumbar support member as a unit to the base so that the torso/cervical spine support member and the pelvic/lumbar support member are pivotable as a unit about a generally horizontal axis extending generally transversely of the table.

5. The therapeutic table of claim 1 futher including limit rod means operatively connected to the pelvic/-lumbar support member for allowing circumductive movement of the pelvic/lumbar support member while preventing rotation of the pelvic/lumbar support member about the axis of the second member of the shaft.

6. The therapeutic table of claim 1 wherein the upper torso/cervical spine support member is rotatably mounted to the base to permit rotation about a generally vertical axis to induce lateral flexion of the patient's spine.

7. The therapeutic table of claim 1 including slidable mounting means for slidably supporting the torso/cervical support member on the base, permitting the torso/cervical support member to slide freely longitudinally of the table as the patient's torso moves in response to the circumductive motion of the pelvic/lumbar spine support member.

8. A therapeutic table for manipulation of the spine of a patient supported thereon comprising:

- a base;
- a frame pivotally mounted to the base for tilting about a generally horizontal axis;
- a forwardly extending upper torso/cervical spine support member mounted on the frame and being positionable with respect thereto;
- a first shaft member mounted to the frame for rotation about a fixed axis, having one end extending rearwardly of the frame;
- a first plate fixed to the rearwardly extending end of the first shaft member;
- a second plate hingedly attached to the first plate;
- adjustable spacer means for adjusting the relative angle between the plates;
- a second shaft member fixed to the second plate oppositely of the first plate;
- a pelvic/lumbar spine support member rotatably fixed to the second shaft member oppositely of the second plate; and
- means for rotating the first shaft member so that when the adjustable spacer means is adjusted to a non-zero angle between the axes the second shaft member and the associated pelvic/lumbar support member moves in a circumductive motion.

9. A therapeutic table for manipulation of the spine of a patient supported thereon, comprising:

- a base and a tiltable frame carried on the base, the frame being tiltable about a generally horizontal axis extending generally transversly of the base;
- an upper torso/cervical spine support member supported on the frame;
- an articulated shaft having a drive shaft member mounted to the frame for rotation about an axis that is fixed with respect to the frame, and a driven shaft member, the drive shaft having an axial bore at least partially therethrough;
- a hinge joining the drive shaft to the driven shaft;
- adjustment means for adjusting the relative angle between the respective axes of the drive shaft and the driven shaft, and the adjustment means comprising a rod slidably disposed in the bore of the drive shaft, the rod being operatively attached at a first end to the driven shaft and including means for adjusting the longitudinal position of the rod with respect to the drive shaft to thereby adjust the angle between the axes of the shaft members;
- a pelvic/lumbar spine support rotatably attached to the driven shaft; and
- means for rotating the drive shaft so that when the adjustment means is adjusted to a non-zero angle between the shaft axes the driven shaft and the associated pelvic/lumbar support move in a circumductive motion.

10. A therapeutic device for manipulation of selected body portions or a patient supported thereon, comprising:

- a first body portion support on which first portion of the patient is to be supported, the first body portion support defining a plane;
- a second body portion support that is adapted to simultaneously support a second portion of the patient, and
- circumductive rotation means, including drive means being a rotating shaft connecting the first and second body portion supports such that the second body portion support rotates circumductively about an axis which is substantially parallel to the plane defined by the first body portion support and the rotating shaft.

11. The therapeutic device of claim 10 wherein the second body portion support rotates at a fixed circumductive angle with respect to the axis, such that as the second body portion support rotates circumductively about the axis, the motion of the first and second body portion supports relative to each other provides therapeutic exercise and manipulation of the spine.

12. The therapeutic device of claim 11 wherein circumductive angle at which the second body portion support rotates circumductively about the axis is adjustable to a plurality of fixed angles to allow for control of the therapeutic exercise and manipulation of the spine.

13. The therapeutic device of claim 12 wherein the angle is adjustable while the therapeutic device is operating.

14. The therapeutic device of claim 10 wherein the circumductive rotation means comprises:

- an articulated shaft having first and second members, the first member having an axis and being constructed and arranged for rotation about that axis,
- a hinge joining the first member and the second member, and
- adjustment means for adjusting the relative angle between the first member and the second member, whereby the second member rotates circumductively around the axis of the first member upon rotation of the articulated shaft, thereby providing therapeutic exercise and manipulation of the spine.

15. The therapeutic device of claim 10 wherein the first body portion support is adapted to support upper torso of a patient and the second body portion support is adapted to support the lower torso of a patient.

16. The therapeutic device of claim 10 wherein the angle at which the second body portion support rotates circumductively about the axis is adjustable to a plurality of fixed angles to allow for control of the therapeutic exercise and manipulation between the first and second portions.

17. The therapeutic device of claim 10 wherein the device is tipped to aid in the therapeutic exercise and manipulation of the first and second body portions.

18. A therapeutic device for manipulation of selected body portions of a patient supported thereon, comprising:

a first body portion support on which a first portion of patient is to be supported, the first body portion support defining a plane and which is constructed and arranged for support of the upper torso and cervical spine;

a second body portion support that is adapted to simultaneously support a second portion of the patient and which is constructed and arranged for support of the pelvic area, and circumductive rotation means connecting the first and second body portion supports such that the second body portion support rotates circumductively about an axis which is substantially parallel to the plane defined by the first body portion support, such that as the second body portion support rotates circumductively about the axis, the motion of the first and second body portion supports relative to each other provides therapeutic exercise and manipulation of the spine.

19. The therapeutic device of claim 18 wherein the angle at which the second body portion support rotates circumductively about the axis is adjustable to allow for control of the therapeutic exercise and manipulation of the spine.

20. The therapeutic device of claim 19 wherein the angle is adjustable while the therapeutic device is operating 21. The therapeutic device of claim 18 wherein the angle at which the second body portion support rotates circumductively about the axis is adjustable to a plurality of fixed angles to allow for control of the therapeutic exercise and manipulation of the spine.

22. The therapeutic device of claim 18 wherein the device is tipped such that the weight of the patient stretches the spine to aid in the therapeutic exercise and manipulation of the spine.

23. A therapeutic device for manipulation of selected body portions of a patient supported thereon, comprising:

a first body portion support on which a first portion of the patient is to be supported;

a second body portion support that is adapted to simultaneously support a second portion of the patient, the second body portion support being constructed and arranged to receive a patient kneeling thereon, and circumductive rotation means connecting the first and second body portion supports such that the second body portion support rotates circumductively relative to the first body portion support.

24. The therapeutic device of claim 23 wherein the angle at which the second body portion support rotates circumductively about the axis is adjustable to allow for control of the therapeutic exercise and manipulation of the spine.

25. The therapeutic device of claim 24 wherein the angle is adjustable while the therapeutic device is operating.

26. The therapeutic device of claim 23 wherein the angle at which the second body portion support rotates circumductively about the axis is adjustable to a plurality of fixed angles to allow for control of the therapeutic exercise and manipulation of the spine.

27. The therapeutic device of claim 23 wherein the device is tipped such that the weight of the patient stretches the spine to aid the therapeutic exercise and manipulation of the spine and wherein the second body portion support is l-shaped to kneelingly receive the patient.

28. A therapeutic device for manipulation of selected body portions of a patient supported thereon, comprising:

a first body portion support having means for supporting the upper torso and cervical spine;

a second body portion support, separate and independent of the first body portion support, having means for simultaneously supporting the lower torso of the patient, including the pelvic area, lumbar spine, and legs, and means for imparting a circumducting motion between the first and second body supports, whereby the circumducting motion of the first and second body portion supports relative to each other provides therapeutic exercise and manipulation of the spine.

29. The therapeutic device of claim 28 wherein the first and second body supports are arranged at an angle to each other and where the angle is adjustable to allow for control of the therapeutic exercise and manipulation of the spine.

30. The therapeutic device of claim 29 wherein the angle is adjustable while the therapeutic device is operating.

31. The therapeutic device of claim 28 wherein the means for imparting a circumducting motion comprises:

an articulated shaft having first and second members, the first member having an axis and being constructed and arranged for rotation about that axis, a hinge joining the first member and the second member, and adjustment means for adjusting the relative angle between the member and the second member, whereby the second member rotates circumductively around the axis of the first member upon rotation of the articulated shaft, thereby providing therapeutic exercise and manipulation of the spine.

32. The therapeutic device of claim 28 wherein the second body portion support is constructed and arranged for kneelingly receiving the patient.

33. The therapeutic device of claim 28 wherein the angle at which the second body portion support rotates circumductively about the axis is adjustable to a plurality of fixed angles to allow for control of the therapeutic exercise and manipulation of the spine.

34. The therapeutic device of claim 28 wherein the device is tipped such that the weight of the patient stretches the spine to aid in the therapeutic exercise and manipulation of the spine.

35. A therapeutic device for manipulation of selected body portions of a patient supported thereon, comprising:

a first body portion support on which a first portion of the patient is to be supported;

a second body portion support that is adapted to simultaneously support a second portion of the patient, and circumductive rotation means connecting the first and second body portion supports such that the second body portion support rotates circumductively about the first body portion support and wherein the second body portion support rotates at an adjustably fixed circumductive angle with respect to the first body portion support, such that as the second body portion support rotates circumductively about the first body portion support, the motion of the first and second body portion supports relative to each other provides therapeutic exercise and manipulation between the first and second body portions, and wherein the adjustably fixed circumductive angle allows for control of the therapeutic exercise and manipulation between the first and second body portions.

36. The therapeutic device of claim 35 wherein the circumductive angle is adjustable while the therapeutic device is operating.

37. The therapeutic device of claim 35 wherein the device is tipped to aid in the therapeutic exercise and manipulation between the first and second body portions.

* * * * *

UNITED STATES PATENT AND TRADEMARK OFFICE

CERTIFICATE OF CORRECTION

PATENT NO. : 5,362,302

DATED : November 8, 1994

INVENTOR(S) : Robert J. Jensen

It is certified that error appears in the above-indentified patent and that said Letters Patent is hereby corrected as shown below:

Col. 5, line 30, delete "ye" and insert -- yet --

Col. 10, line 18, before "first" insert -- a --

Col. 12, line 7, delete :1-shaped" and insert -- L-shaped --

Signed and Sealed this

Thirty-first Day of January, 1995

Attest:

Bruce Lehman

BRUCE LEHMAN

*Attesting Officer*

*Commissioner of Patents and Trademarks*